US007485290B2

(12) United States Patent
Ushida et al.

(10) Patent No.: US 7,485,290 B2
(45) Date of Patent: Feb. 3, 2009

(54) COMPOSITIONS CONTAINING BACTERIUM CAPABLE OF CONVERTING LACTIC ACID INTO BUTYRIC ACID AND METHOD OF PREVENTING/TREATING HYPERLACTIC ACIDEMIA IN DIGESTIVE TRACT AND COLON CANCER BY USING THE SAME

(75) Inventors: Kazunari Ushida, Hyogo (JP); Takamitsu Tsukahara, Hyogo (JP); Masaaki Okada, Osaka (JP); Hironari Koyama, Osaka (JP)

(73) Assignees: Kyodoken Institute for Animal Science Research & Development, Kyoto-shi (JP); Combi Corporation, Tokyo (JP)

( * ) Notice: Subject to any disclaimer, the term of this patent is extended or adjusted under 35 U.S.C. 154(b) by 0 days.

(21) Appl. No.: 10/474,000

(22) PCT Filed: Apr. 5, 2002

(86) PCT No.: PCT/JP02/03460

§ 371 (c)(1), (2), (4) Date: Feb. 24, 2004

(87) PCT Pub. No.: WO02/080947

PCT Pub. Date: Oct. 17, 2002

(65) Prior Publication Data

US 2004/0120963 A1 Jun. 24, 2004

(30) Foreign Application Priority Data

Apr. 6, 2001 (JP) ............................ 2001-108970

(51) Int. Cl.
*A01N 63/00* (2006.01)
*C12N 1/12* (2006.01)

(52) U.S. Cl. .................... 424/93.1; 435/243; 435/252.1

(58) Field of Classification Search ............. 424/184.1, 424/93.1; 435/243
See application file for complete search history.

(56) References Cited

U.S. PATENT DOCUMENTS

| | | | | |
|---|---|---|---|---|
| 4,138,498 | A * | 2/1979 | Das | 426/2 |
| 5,308,615 | A | 5/1994 | DeLoach et al. | |
| 5,380,525 | A * | 1/1995 | Leedle et al. | 424/93.4 |

FOREIGN PATENT DOCUMENTS

| | | |
|---|---|---|
| EP | 0 456 418 A2 | 11/1991 |
| JP | 6-197774 | 7/1994 |
| WO | 99/00136 | 1/1999 |
| WO | 01/87317 | * 11/2001 |

OTHER PUBLICATIONS

Kung et al. ,Journal of Animal Science vol. 73, pp. 250-256, 1995.*
Counotte et al. ,Applied and Evironmental Microbiology, vol. 42, No. 4, pp. 649-655, 1981.*
Tsao et al. chemoprevention of cancer, CA Cancer Journal for clinicians, vol. 54, pp. 150-180, 2004.*
American Type Culture Collection Catalogue, 17th Edition, 1989, p. 126.*
Wallace et al (Letters in Applied Microbiology, 3(2):23-26, 1986).*
Machine translation of JP, 01/087317 (2001).*
Counotte, G. et al., "Role of Megasphaera elsdenii in the fermentation of DL-[2-$^{13}$ C] lactate in the rumen of dairy cattle", Appl. Environ. Microbiol.,vol. 42, No. 4, pp. 649-655 1981.
P. Broebech Mortensen, et al., "Short-Chain Fatty Acids in the Human Colon: Relation to Gastrointestinal Health and Disease", Scandinavian Journal of Gastroenterology Supplement, No. 216, XP-008024700, 1996, pp. 132-148.
Database Biosis 'Online!, AN-PREV198987035415, XP-002325812, P. Vernia, et al., "Fecal Lactate and Ulcerative Colitis", 1988, 1 page.

* cited by examiner

*Primary Examiner*—Patricia A Duffy
(74) *Attorney, Agent, or Firm*—Oblon, Spivak, McClelland, Maier & Neustadt, P.C.

(57) ABSTRACT

A composition comprising *Megasphaera elsdenii* strain JCM1772 or strain iNP-001. The compositions may optionally contain live or processed bacterial products. A method for decreasing lactate production or increasing butyric acid production or for treating a disease associated with hyperlactate production in a non-ruminant using *Megasphaera elsdenii.*

12 Claims, No Drawings

COMPOSITIONS CONTAINING BACTERIUM CAPABLE OF CONVERTING LACTIC ACID INTO BUTYRIC ACID AND METHOD OF PREVENTING/TREATING HYPERLACTIC ACIDEMIA IN DIGESTIVE TRACT AND COLON CANCER BY USING THE SAME

TECHNICAL FIELD

This invention relates to a composition containing bacteria. More particularly, it relates to a composition or pharmaceutical composition for human or animals which comprises as an active ingredient bacteria or processed product thereof capable of converting lactic acid into butyric acid, and a food or feed containing the composition, as well as a method for preventing or treating hyperlactate production in digestive tract and colon cancer in human beings or animals by using the same.

BACKGROUND ART

It has been known that at the time of onset of short-bowel syndrome, ulcerative colitis, diarrhea caused by antibiotics, dyspeptic diarrhea, or Crohn's disease, or after excision of a digestive tract and administration of an elemental diet, fermentation in the large intestine becomes abnormal, accompanied by high accumulation of lactic acid.

Since lactic acid is a strongly acidic substance and sparingly absorbed in the large intestine, once it becomes in an excess state, the inside of the large intestine is quickly acidified. In such a state, the lactic acid conversion function of bacteria and the epithelial cell function in absorption are inhibited thereby lowering the consumption of lactic acid. As a result, accumulation of lactic acid is accelerated and results in repetition of a vicious circle, which makes recovery from pathological conditions difficult.

Heretofore, in such an abnormal physiology of the colon, it has been usually to administer a pharmaceutical product of lactobacilli, bifidobacteria or enterococci, or to administer oligosaccharides to activate these bacteria.

These bacteria, however, are lactic acid bacteria in the broad sense, which produce lactic acid as a major product. Therefore, it is doubtful whether they are effective to cure diseases caused by abnormal accumulation of lactic acid.

On the other hand, butyric acid which is one of short-chain fatty acids is produced by normal fermentation in the large intestine and utilized selectively by the epithelium of the colonic mucosa. Though lactic acid is sparingly absorbed from the epithelial cell of the colonic mucosa and cannot be utilized as an energy source in the mucosal epithelial cells, butyric acid works as an energy source to stimulate the growth of the epithelial cells on the colonic mucosa and promote absorption of minerals and water.

Therefore, supply of not lactic acid but butyric acid is essential in order to develop soundly the function of the colonic mucosa.

In addition, it is known that the butyric acid content is decreased in the digestive tract in a patient suffering from colon cancer. On the other hand, it is known that butyric acid promotes differentiation of the cells of colon cancer to reduce the number of cancer cells; therefore, it can be said that increase of butyric acid in the digestive tract is advantageous in case of such a disease.

Thus, it cannot be said that a method for positively eliminating the state of accumulation of lactic acid and a technique for quickly converting lactic acid into a useful substance by using a lactic acid bacterium preparation or activator have been established. Moreover, materials used for the purpose of improving the internal environment of the intestine do not reduce hyperlactate production or help to generate butyric acid.

The present invention was made in view of the above-mentioned problems in the prior art. The purpose of the invention, accordingly, is to provide a method for quickly converting lactic acid into butyric acid in the intestine, and thus to alleviate pathological conditions due to abnormal accumulation of lactic acid and by increase of butyric acid make much more effective the prior means for improving the intestinal environment which aim to improve the intestinal environment and activate lactic acid bacteria.

DISCLOSURE OF INVENTION

The present inventors had attempted various methods for converting lactic acid into butyric acid and found that a certain bacterium isolated from the intestinal tract had the aimed function. Thus, the invention was completed.

According to the invention, a composition or pharmaceutical composition for human or animals which contains as an active ingredient bacteria or processed product thereof capable of converting lactic acid into butyric acid, and a food or feed containing the composition, as well as a method for preventing or treating hyperlactate production in digestive tract and colon cancer in human or animals using the same, are provided.

BEST MODE FOR CARRYING OUT THE INVENTION

The bacteria used in the invention include those which are able to convert lactic acid into butyric acid, though the action mechanism has not yet been elucidated, for example, bacteria belonging to the genus *Megasphaera* or *Mitsuokella,* or *Butyrivibrio fibrisolvens, Fusobacterium* and *Clostridium.*

Among them, *Megasphaera elsdenii* or *Mitsuokella multiacida* which produces butyric acid from lactic acid by an enzymatic reaction is preferred.

These bacteria are able to convert lactic acid into butyric acid in a state of being sufficiently capable of exerting their biological activities under normal conditions, that is, in a living state.

Therefore, the bacteria of the invention may be those processed by various known methods in the art, such as lyophilization or ultrasonic disintegration of bacteria, or bacteriolysis, as long as they maintain such function.

The above-mentioned bacteria are able to convert an excess quantity of lactic acid occurring in the large intestine of human or animals into butyric acid. According to the experiment conducted by the inventors, when acetic acid is present in addition to lactic acid, the conversion of lactic acid by bacteria is promoted to produce a larger quantity of butyric acid.

Since acetic acid is an organic acid present ubiquitously in the large intestine, it is considered that lactic acid will more quickly be converted into butyric acid by the above-mentioned bacteria in the large intestine.

According to the present invention, therefore, a composition which contains as an active ingredient bacteria or processed product thereof capable of converting lactic acid into butyric acid is provided. The said composition can be used as a pharmaceutical composition for human or animals in prevention or treatment of hyperlactate production occurring in short-bowel syndrome, ulcerative colitis, diarrhea caused by antibiotics, dyspeptic diarrhea, and Crohn's disease, or hyperlactate production occurring after excision of a digestive tract or administration of elemental diet, or colon cancer.

The composition of the present invention may be prepared in a conventional manner using known solid or liquid excipients in the art solid excipients include, for example, lactose, sucrose, glucose, corn starch, gelatin, starch, dextrin, calcium phosphate, calcium carbonate, synthetic or natural aluminum silicate, magnesium oxide, dry aluminum hydroxide, magnesium stearate, sodium bicarbonate, and dry yeast. Liquid excipients include, for example, water, glycerin, propylene glycol, simple syrup, ethanol, fatty oil, ethylene glycol, polyethylene glycol, and sorbitol.

The composition of the present invention if desired may contain a conventional additive or additives such as buffer, stabilizer, sweetener, adherent lubricating agent, antiseptic, anti-fungal agent, anti-oxidant, pigment, and flavor, or a pharmaceutically active ingredient or ingredients such as anthelmintics and enzymes. The composition may be formulated into a desired form such as fine granules, powders, granules, liquids and solutions, tablets, emulsions, capsules, chewable preparations, and so on.

The composition of the invention prepared with a variety of the above-mentioned excipients and additives can be added by mixing or spraying to the raw materials, intermediates or end products of foods or animal feeds to give the aimed foods or feeds which are expected to be effective in prevention or treatment of hyperlactate production and colon cancer.

Therefore, according to the invention, a method for preventing or treating hyperlactate production and colon cancer inhuman or animals, for example, cattle, swine, equine, sheep, goat, chicken, wild duck, turkey, domestic duck, goose, ostrich, as well as pet animals such as dog, cat, parakeet, or pigeon, which method comprises administering the above-mentioned composition or food or feed, is proveded.

The foods or feeds containing the composition of the invention may be taken in the conventional way, respectively.

The foods include solid or liquid or semisolid products, for example, confectionary such as candy, cookies, jelly or yogurt, soft drink, nutrient drink, soup, and like.

The feeds include foods for animals other than human, specifically, rice, wheat, milo, soybean meal, wheat bran, defatted rice bran, fish meal, skim powdered milk, dry whey, oil and fat, alfalfa meal, northern sea meal, soybean fat and oil, powdered refined beef fat, wheat flour, rapeseed oil, meat and bone meal (feather meal), animal fat and oil, calcium phosphate, corn gluten meal, molasses, corn germ meal, calcium carbonate, tricalcium phosphate, sodium chloride, choline chloride, vitamins (vitamin A, vitamin $B_1$, vitamin $B_2$, vitamin $B_6$, vitamin $B_{12}$, vitamin D, vitamin E, calcium pantothenate, nicotinic acid amide, folic acid, etc.), amino acids (lysine, methionine, etc.), trace inorganic salts (magnesium sulfate, iron sulfate, copper sulfate, zinc sulfate, potassium iodide, cobalt sulfate, etc.), and the like These may be properly admixed into feeds or drinking water.

The composition of the invention, when used for pharmaceutical purposes, may be used in a dose of $10^4$-$10^{10}$ cells/60 kg/day, preferably $10^6$-$10^9$ cells/60 kg/day, for both of human and animals, though it depends on the condition of the health and the age of the human or animal to be treated for prevention or treatment.

The composition when used as a mixture with a food or feed may be used in an amount of $10^2$-$10^3$ cells/g, which is considered to have no influence on the taste and appearance of the food or feed.

EXAMPLES

The invention is explained below in details by the examples, but the invention is not limited to these examples. The following abbreviations are used in the examples below:
PY: Peptide-Yeast extract broth,
PYF: Peptide-Yeast extract broth with Fildes solution, and
BL medium: Blood-liver agar.

Example 1

Isolation of Butyric Acid Producing Bacteria

The cecal content collected from a swine (cross breeding adult sow given cecostomy) was inoculated on a PYF medium (Tomotari Mitsuoka, A Colon Atlas of Anaerobic Bacteria, Sobun-sha, Tokyo, p.325, 1980) to which 1.0% (w/v) sodium gluconate (Fujisawa Pharm. Co.) as a substrate was added or on a PYF medium containing no sodium gluconate and subjected to enrichment culture (39° C., for 144 hours, anaerobic culture).

Subsequently, the enrichment cultured broth was inoculated on an anaerobic non-selective plate (BL medium, Nissui Co.) and incubated under anaerobic conditions at 39° C. for 48 hours, strains growing only on a sodium gluconate-added PYF medium were selected according to their colony morphotype, and a colony thereof was isolated.

The selected strain was inoculated on a sodium gluconate-added PYF medium and on a medium containing no sodium gluconate and incubated anaerobically at 39° C. for 48 hours. The reaction was stopped with addition of 6N hydrochloric acid, and the concentration of organic acids in the culture broth was determined by ion-exclusion high performance liquid chromatography (by Waters, hereinafter referred to as HPLC). Pretreatment and HPLC were carried out in the same condition described in Ushida and Sakata, Anim. Sci. Technol., 69, 571-575 (1988).

Based on the result of the measurement, two strains were selected with the productivity of butyric acid as the indicator.

The two strains were inoculated on a PYF medium and incubated in an anaerobic condition at 39¢ C. for 48 hours. From the resulting cells, 16 S rDNA was extracted and sequenced by Li-CCR LIC-4200L(S)-2 (Aloka). The sequence was analyzed by Base Image IR ver.4 (Aloka) and compared with the 16 S rDNA sequence of the known bacteria according to the Gene Bank database by BLAST software.

As a result, one of the strains was 98% homologous to *Megasphaera elsdenii* ATCC 17752 and identified as *Megasphaera elsdenii*. The other strain was positioned between genus *Mitsuokella* and *Selenomonas* according to it's morophology, but it was 94% homologous to *Mitsuokella multiacida* NCTC 10934 and determined to be related to the said strain.

Example 2

Assay of Lactic Acid Availability of Butyric Acid Producing Bacteria

The isolated two strains and an analogous strain *Megasphaera elsdenii* JCM 1772 (obtained from Institute of Physical and Chemical Research) were incubated on a PY medium (basic PYF medium from which Fildes solution was removed) to which 10 mM lactic acid (Wako Pure Chemical Industries ltd.) was added and on a medium to which lactic acid and acetic acid 10 mM each (Wako Pure Chemical) were added, under anaerobic conditions at 37° C. After 24 hours incubation, the lactic acid concentration of the culture media was measured by ion-exclusion HPLC (Waters). Pretreatment and HPLC were carried out in the same conditions as described in Ushida and Sakata, Anim. Sci. Technol., 69, 571-575 (1988).

TABLE 1

| | Butyric Acid Conc. (mM) | | |
|---|---|---|---|
| | Isolated Strain | | Analogous Strain |
| Medium | *Megasphaera elsdenii* | *Mitsuokella multiacida* | *Megasphaera elsdenii* JCM1772 |
| PY medium | 0.65 ± 0.31 | 1.04 ± 0.81 | 6.63 ± 0.69 |
| 10 mM LA*-PY medium | 1.32 ± 0.66 | 0.91 ± 1.01 | 8.43 ± 0.68 |
| 10 mM LA & AA**-PY medium | 1.11 ± 0.73 | 4.57 ± 1.06 | 11.94 ± 1.04 |

*LA: Lactic acid;
**AA: Acetic acid

As shown in Table 1, all of the strains showed high rates of production of butyric acid by addition of lactic acid or lactic acid and acetic acid. Thus, it was elucidated that these strains could utilize lactic acid or lactic acid and acetic acid to produce butyric acid.

Example 3

Assay of the Action of Butyric Acid Producing Bacteria Against a Diarrhea Symptom Caused by Accumulation of Lactic Acid To a rat to which an easily fermentable substrate fructo-oligosaccharides was given multiple times to cause a diarrhea symptom was orally administered *Megasphaera elsdenii* to examine whether the diarrhea symptom disappeared.

As for test animals, pregnant rats of Wistar family (purchased from Japan SLC) were allowed to give birth in a laboratory (non-barrier system environment), and one of the grown rats (6 weeks of age) was used.

10% Fructo-oligosaccharides (FOS) feed comprised of 20% casein, 54% α-corn starch, 5% cellulose, 5% soybean oil, 1% vitamin mixture, 5% mineral mixture and 10% fructo-oligosaccharides (fructo-oligosaccharides from Meiji Seika; and others from Oriental Yeast) was fed freely in a powder form during the test period. Drinking water was given freely through the entire test period.

*Megasphaera elsdenii* JCM 1772 (obtained from Institute of Physical and Chemical Research) was inoculated in a liquid medium comprised of 41.7 g/L of modified GAM broth (Nissui Pharmaceutical), 10 g/L of glucose, 0.4 ml/L of resazurin, 0.5 g/L cysteine hydrochloride, and 5 g/L of $NaHCO_3$, and incubated for growth under anaerobic conditions at 37° C. for 24 hours to give a solution of bacterium for administration. The number of bacteria after incubation was $2\times10^8$ cfu/ml.

From the beginning of the feeding of 10% FOS, the rectal feces were recovered at from 21 to 24 o'clock everyday in order to observe the appearance of feces and determine the concentration of various organic acid contained in the feces by ion exclusion HPLC. Pretreatment and HPLC were carried out in the same conditions described in Ushida and Sakata, Anim. Sci. Technol., 69, 100-107 (1998).

As a result, a diarrhea symptom was observed at the day 3 after the beginning of the feeding of 10% FOS, and the diarrhea was continuously recognized. Accordingly, from the day 7 after the beginning of the feeding of 10% FOS, 1 ml of the solution of bacterium was administered orally through stomach sonde at 17 o'clock everyday for 3 days.

Table 2 shows the result of feces appearance and Table 3 shows the change of the concentration of organic acid contained in the rectal feces.

TABLE 2

| | Days after feeding of 10% FOS | | | | | | | | | |
|---|---|---|---|---|---|---|---|---|---|---|
| | 0 | 1 | 2 | 3 | 4 | 5 | 6 | 7 | 8 | 9 |
| Feces Appear. | Normal | Normal | Normal | Diarrhea | Diarrhea | Diarrhea | Diarrhea | Diarrhea | Normal | Normal |

TABLE 3

| Days after | Detected organic acids (mmol/kg wet feces) | | | | | | | | | |
|---|---|---|---|---|---|---|---|---|---|---|
| Feed start* | Succinic acid | Lactic acid | Formic acid | Acetic acid | Propionic acid | i-Butyric acid | Butyric acid | i-Valeric acid | Valeric acid | Total** |
| 0 | 3.13 | 1.19 | 0.29 | 28.52 | 7.27 | 0.93 | 1.25 | 0.00 | 0.00 | 37.97 |
| 1 | 4.98 | 121.43 | 0.00 | 5.19 | 0.73 | 0.00 | 1.25 | 0.00 | 0.00 | 7.18 |
| 2 | 0.93 | 84.88 | 0.00 | 10.77 | 2.13 | 1.59 | 1.48 | 0.00 | 0.00 | 15.97 |
| 3 | 0.38 | 131.56 | 0.00 | 5.43 | 0.80 | 0.00 | 0.00 | 0.00 | 0.00 | 6.23 |
| 4 | 1.08 | 143.96 | 0.00 | 7.40 | 0.00 | 0.00 | 0.67 | 0.53 | 0.00 | 8.60 |
| 5 | 0.48 | 135.98 | 0.00 | 8.89 | 0.00 | 2.09 | 0.00 | 0.00 | 0.00 | 10.99 |
| 6 | 0.50 | 118.08 | 0.00 | 7.76 | 0.00 | 0.00 | 3.37 | 0.00 | 0.00 | 11.13 |
| 7 | 0.83 | 134.37 | 0.00 | 8.43 | 1.01 | 1.24 | 3.43 | 0.00 | 0.00 | 14.11 |
| 8 | 5.36 | 17.74 | 0.42 | 13.11 | 1.98 | 0.00 | 6.25 | 0.00 | 0.00 | 21.35 |
| 9 | 2.53 | 12.26 | 0.00 | 14.29 | 1.07 | 0.00 | 14.84 | 0.00 | 4.34 | 34.54 |

*Days after feeding of 10% FOS
**Total of acetic acid, propionic acid, isobutyric acid, butyric acid, isovaleric acid and valeric acid As shown in Table 2, the diarrhea symptom disappeared the day after the beginning of administration of the bacterial solution. As shown in Table 3, it was seen that the concentration of lactic acid drastically decreased and butyric acid increased.

Example 4

Assay of the Action of Butyric Acid Producing Bacteria Against an Hyperlactate Production in the Digestive Tract.

In rats, fructo-oligosaccharides were excessively taken to artificially increase the lactic acid concentration in the large intestine. *Megasphaera elsdenii* was orally administered to the rats to elucidate the effect of this bacterium against accumulation of lactic acid.

As test animals, 12 male SD rats of 6 weeks of age (SPF grade; purchased from Japan SLC) were used.

Rats were individually taken in the rat cage kept in temperature controlled room, and they acclimatized to the facilities for 6 days. During acclimatization, commercially available rat chow (Labostock MR; Nippon Nosan Kogyo) and drinking water were given freely.

After the completion of acclimatization, 10% fructo-oligosaccharide (FOS) feed comprising the same composition as in Example 3 was fed freely.

*Megasphaera elsdenii* JCM 1772 (obtained from Institute of Physical and Chemical Research) was inoculated on a culture medium of the composition shown in Table 4, and incubated under anaerobic conditions at 37° C. for 24 hours. The cell number of *Megasphaera elsdenii* JCM 1772 after incubation and harvested by centrifugation was $2.7 \times 10^{13}$ CFU/mL, which was administered as bacteria solution.

TABLE 4

| Composition of the liquid culture medium for *Megasphaera elsdenii* (per 1 L) | |
|---|---|
| Hungate solution A*1 | 340 mL |
| Hungate solution B*2 | 340 mL |

TABLE 4-continued

| Composition of the liquid culture medium for *Megasphaera elsdenii* (per 1 L) | |
|---|---|
| Trypticase | 1 g |
| Yeast extract | 0.5 g |
| Glucose | 2 g |
| Distilled water | 320 mL |
| Resazurin | 0.4 mL |
| L-Cysteine hydrochloride | 0.5 g |
| $NaHCO_3$ | 5 g |

*1Hungate solution A (per 1 L): 6 g NaCl; 1 g $NaHCO_3$; 1 g $KH_2PO_4$; 0.2 g $MgSO_4$; 0.1 g $CaCl_2$

*2Hungate solution B (per 1 L): 3 g $K_2HPO_4$

Animals were divided at random into 2 groups, that is, 5 rats to which *Megasphaera elsdenii* was administered and 7 rats as a control group to which no administration was made. To the group to which *Megasphaera elsdenii* was administered was administered the above-prepared bacterium solution at the day 3 after the beginning of feeding with 10% FOS everyday at 10 o'clock for 3 days at a dose of 0.5 mL/rat orally through a stomach sonde. To the control group to which *Megasphaera elsdenii* was not administered was administered physiological saline in the same manner.

From the beginning of the feeding of 10% FOS, the rectal feces were recovered at 17 o'clock everyday in order to determine the concentration of organic acids contained in the feces by ion exclusion HPLC. Pretreatment and HPLC were carried out in the same condition as described in Ushida and Sakata, Anim. Sci. Technol., 69, 100-107 (1998). After the lapse of 3 days from the beginning of administration of bacteria solution, all rats were killed and the cecal content was collected to determine the concentration of organic acids.

The concentration of organic acids were tested by the Student's t-test or Welch's t-test, where $P<0.05$ indicating a significant difference.

Table 5 shows the change of the organic acid concentration in the rectal feces and the cecal contents.

TABLE 5

| | | Unit (mmol/kg wet feces) | | | | | |
|---|---|---|---|---|---|---|---|
| Organic | Test | Days after the beginning of feeding of FOS | | | | | |
| Acid | group | 0 | 1 | 2 | 3 | 4 | 5* |
| Succinic | Adm. group | 9.0 ± 7.9 | 2.2 ± 2.0 | 0.0 ± 0.0 | 2.8 ± 4.2 | 9.0 ± 9.6 | 8.4 ± 7.0 |
| acid | Control | 8.8 ± 9.5 | 3.0 ± 4.9 | 0.3 ± 0.6 | 0.2 ± 0.4 | 4.0 ± 9.2 | 10.0 ± 7.7 |
| Lactic | Adm. group | 52.7 ± 23.8 | 64.5 ± 17.0 | 73.0 ± 20.2 | 37.3 ± 33.7 | 16.7 ± 10.4* | 8.7 ± 19.0* |
| acid | Control | 50.6 ± 18.9 | 81.4 ± 11.8 | 72.7 ± 11.5 | 61.5 ± 24.9 | 39.0 ± 13.2 | 47.1 ± 22.1 |
| Formic | Adm. group | 3.0 ± 1.4 | 4.0 ± 2.1 | 3.5 ± 1.5 | 3.0 ± 2.8 | 1.7 ± 1.5 | 5.7 ± 1.9* |
| acid | Control | 2.9 ± 1.4 | 5.5 ± 3.1 | 3.8 ± 4.5 | 2.7 ± 1.6 | 2.7 ± 1.5 | 3.6 ± 1.1 |
| Acetic | Adm. group | 16.3 ± 8.3 | 12.5 ± 10.6 | 14.1 ± 14.9 | 25.5 ± 26.1 | 22.2 ± 11.4 | 29.8 ± 6.2 |
| acid | Control | 15.2 ± 4.0 | 24.1 ± 24.4 | 13.8 ± 15.3 | 14.0 ± 4.2 | 17.0 ± 4.8 | 21.8 ± 6.9 |
| Propionic | Adm. group | 1.7 ± 1.1 | 1.8 ± 1.0 | 3.1 ± 1.5 | 4.3 ± 1.5 | 2.9 ± 2.3 | 8.4 ± 4.3 |
| acid | Control | 1.3 ± 0.7 | 2.2 ± 1.7 | 2.2 ± 1.2 | 5.0 ± 4.0 | 7.1 ± 4.7 | 14.6 ± 9.8 |
| i-Butyric | Adm. group | 0.2 ± 0.4 | 0.0 ± 0.0 | 0.2 ± 0.3 | 0.1 ± 0.2 | 0.3 ± 0.6 | 1.0 ± 1.2 |
| acid | Control | 0.0 ± 0.0 | 0.3 ± 0.6 | 0.4 ± 0.9 | 0.3 ± 0.7 | 0.6 ± 0.7 | 0.8 ± 1.8 |
| Butyric | Adm. group | 0.5 ± 0.3 | 0.1 ± 0.2 | 0.3 ± 0.3 | 10.6 ± 11.2 | 7.5 ± 4.2* | 35.3 ± 10.2* |
| acid | Control | 0.4 ± 0.4 | 1.7 ± 2.9 | 1.0 ± 2.4 | 0.4 ± 0.6 | 1.0 ± 0.8 | 4.8 ± 4.1 |
| i-Valeric | Adm. group | 0.2 ± 0.3 | 0.4 ± 0.4 | 0.1 ± 0.2 | 0.5 ± 0.7 | 0.3 ± 0.5 | 0.2 ± 0.3 |
| acid | Control | 0.0 ± 0.0 | 0.2 ± 0.3 | 0.3 ± 0.4 | 0.3 ± 0.3 | 0.2 ± 0.3 | 0.0 ± 0.1 |
| Valeric | Adm. group | 0.3 ± 0.5 | 0.3 ± 0.5 | 0.0 ± 0.0 | 1.1 ± 1.2 | 0.3 ± 0.5 | 5.1 ± 1.8* |
| acid | Control | 0.3 ± 0.4 | 0.2 ± 0.3 | 0.1 ± 0.1 | 0.1 ± 0.3 | 0.4 ± 0.4 | 0.1 ± 0.2 |
| Short chain | Adm. group | 19.1 ± 9.2 | 15.1 ± 10.4 | 17.8 ± 14.1 | 42.1 ± 33.4 | 33.6 ± 11.2 | 79.8 ± 10.5* |
| fatty acids** | Control | 17.1 ± 4.6 | 28.8 ± 27.9 | 17.7 ± 17.9 | 20.0 ± 6.2 | 26.3 ± 8.0 | 42.1 ± 20.1 |

*There is a significant difference between the administered (Adm.) group and the control ($P < 0.05$).

**Total of acetic acid, propionic acid, isobutyric acid, butyric acid, isovaleric acid and valeric acid By feeding with 10% FOS, the accumulation of lactic acid by fructo-oligosaccharides were confirmed in the rectal feces in individual cases.

The group to which *Megasphaera elsdenii* was administered showed decrease in lactic acid from the beginning of the administration of bacteria solution, and the difference was remarkable on Day 2 after the beginning of the administration (16.7 vs. 39.0 mmol/kg; with a significant difference). With decrease of lactic acid, the butyric acid concentration increased, 2 days after the beginning of the administration being 750% of the level of the control group (7.5 vs. 1.0 mmol/kg; with a significant difference).

In other organic acids, a statistically significant change was recognized ($p<0.05$).

According to the invention, a composition or pharmaceutical composition for human or animals which contains as an active ingredient bacteria or processed product thereof capable of converting lactic acid into butyric acid, and a food or feed containing the composition, as well as a method for preventing or treating hyperlactate production in digestive tract and colon cancer in human or animals using the same, are provided.

Therefore, using these compositions, it is possible to quickly convert lactic acid into butyric acid in an environment in which lactic acid is accumulated to a unusual degree, and as a result it is possible to prevent safely and effectively a pathological state caused by abnormal accumulation of lactic acid, whereby butyric acid works to improve effectively the diseased state and recover a healthy state of the large intestine.

*Megasphaera elsdenii* strain iNP-001 was deposited under the terms of the Budapest Treaty on Feb. 22, 2005 at the International Depositary Authority (NPMD) at 2-5-8 Kazusakamatari Kisarazu-shi, Chiba-ken 292-0818, Japan.

The invention claimed is:

1. Isolated *Megasphaera elsdenii* strain iNP-001.

2. A non-ruminant food or feed comprising:

a viable microorganism consisting of isolated *Megasphaera elsdenii* strain iNP-001, and at least one food ingredient other than said *Megasphaera elsdenii* strain iNP-001.

3. The food or feed of claim 2, which is a feed formulated for administration to non-ruminant animals.

4. The food or feed of claim 2, which is feed for swine.

5. The food or feed of claim 2, wherein said other food ingredient comprises molasses.

6. The food or feed of claim 2, wherein said other food ingredient comprises rice, wheat, milo, corn gluten meal, soybean meal, alfalfa meal, wheat bran, defatted rice bran, or corn germ meal.

7. The food or feed of claim 2, wherein said other food ingredient comprises fish meal, northern sea meal, meat and bone meal, or feather meal.

8. The food or feed of claim 2, wherein said other food ingredient comprises at least one oil or at least one fat.

9. The food or feed of claim 2, wherein said other food ingredient comprises at least one vitamin, at least one amino acid, or choline chloride.

10. The food or feed of claim 2, wherein said other food ingredient comprises calcium phosphate, calcium carbonate, tricalcium phosphate, or at least one trace inorganic salt.

11. The food or feed of claim 2, wherein said other food ingredient comprises skim milk powder or dry whey.

12. A method for reducing lactate production or increasing butyric acid production in the large intestine of an animal comprising:

feeding the composition of claim 2 in an amount effective to reduce lactate production or increase butyric acid production in the animal.

* * * * *